United States Patent [19]

Shorthill

[11] Patent Number: 5,511,278
[45] Date of Patent: Apr. 30, 1996

[54] CLEANER WITH SCENT DISPENSING

[75] Inventor: Robert C. Shorthill, Canton, Ohio

[73] Assignee: The Hoover Company, North Canton, Ohio

[21] Appl. No.: 222,250

[22] Filed: Apr. 4, 1994

[51] Int. Cl.[6] ............................................. A47L 9/00
[52] U.S. Cl. ............................ 15/246.2; 15/339; 55/279
[58] Field of Search .................... 15/339, 246.2; 55/279

[56] References Cited

U.S. PATENT DOCUMENTS

| | | |
|---|---|---|
| 1,764,127 | 6/1930 | Stolpe . |
| 1,863,883 | 6/1932 | Schneider . |
| 3,844,478 | 12/1972 | Davis ................................................ 239/57 |
| 4,554,698 | 11/1985 | Rennecker et al. .......................... 15/339 |

OTHER PUBLICATIONS

Photos —Hoover® Turbomaster™ cleaner U5080—Received 29 Nov. 1987.
Photos—Hoover® Turbopower™ cleaner U2568—Received 16 Apr. 1989.

*Primary Examiner*—Chris K. Moore

[57] ABSTRACT

A hard bag portion of a vacuum cleaner is provided with a scent dispensing arrangement where suction airflow is valved at the hard bag portion before the downstream disposed scent tablet. It includes a manually actuated loosely mounted, slide member having a pocket for containing a scent tablet. This slide and its pocket move sidewardly to be centered on or offset from a slot in the hard bag through which vacuum cleaner discharge air flows. This air flow impinges directly or indirectly of the scent tablet to provide a flow of lesser or greater scented air which escapes around the loosely mounted slide member.

5 Claims, 3 Drawing Sheets

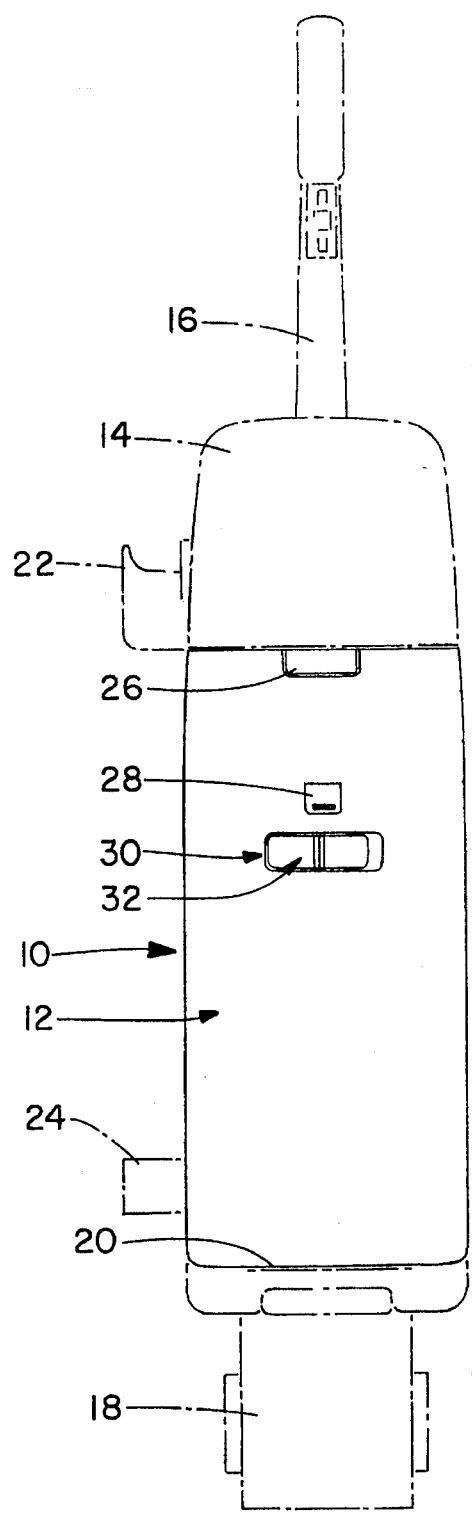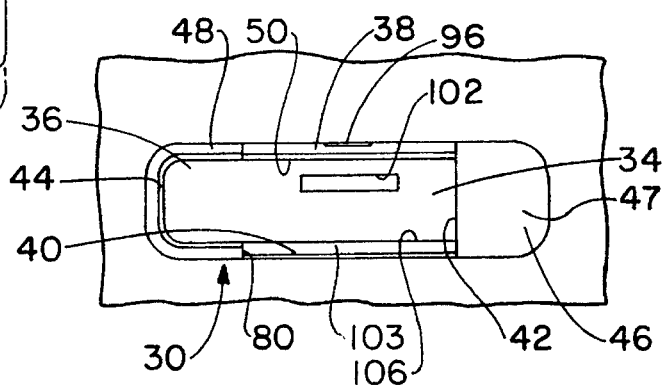

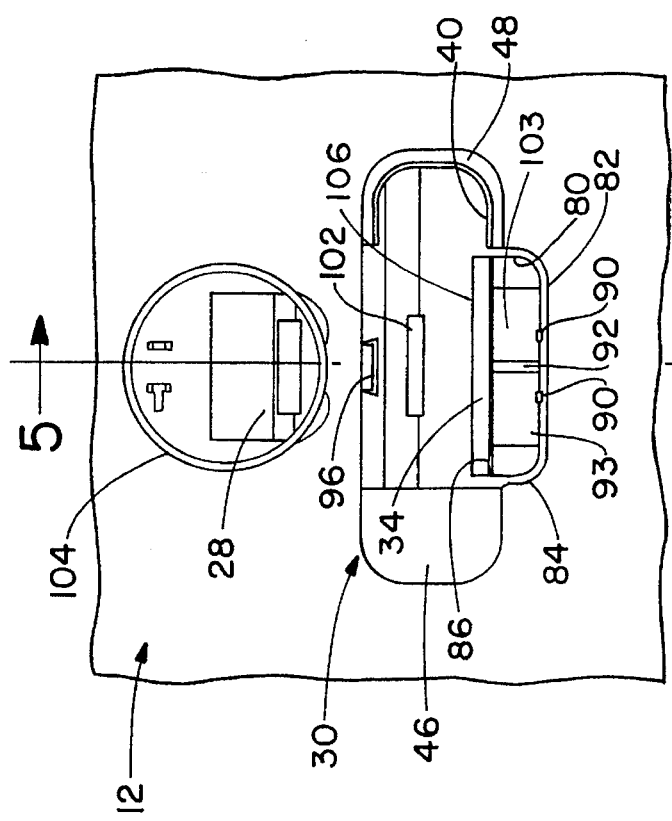
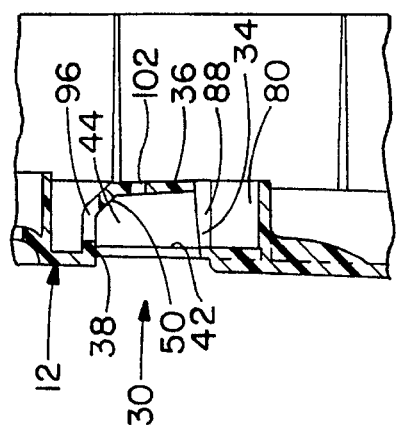
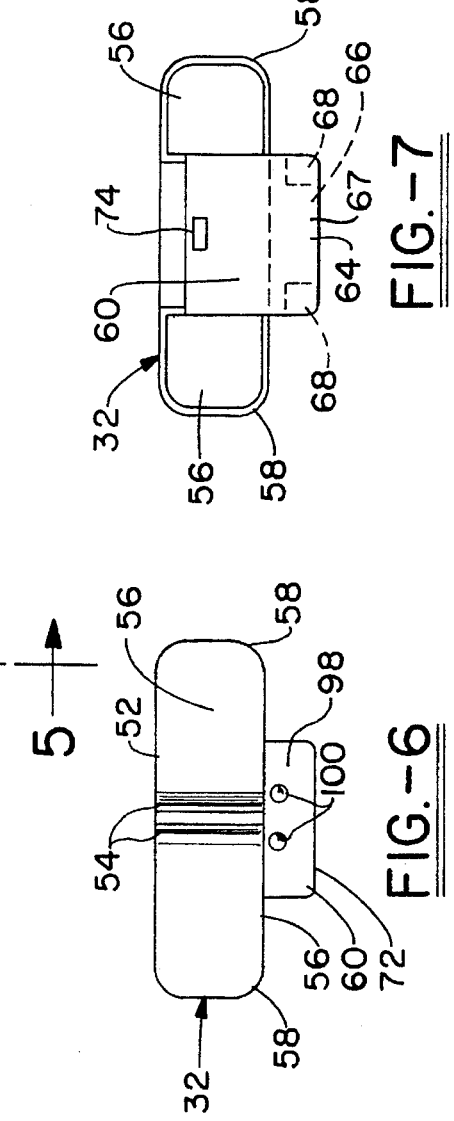
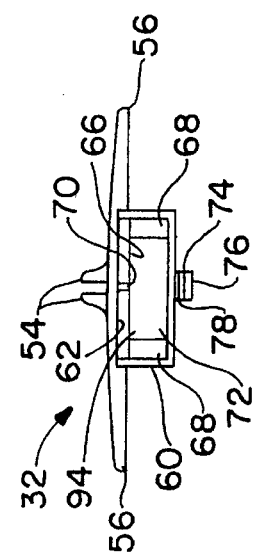

5,511,278

CLEANER WITH SCENT DISPENSING

BACKGROUND OF THE INVENTION

1. Field of the Invention

The present invention relates to vacuum cleaners and, more specifically, to a scent dispenser arrangement usable with a vacuum cleaner.

2. Description of the Prior Art

Scent dispensers utilized, both, for generalized purposes and with vacuum cleaners are old and well known. The ones used with cleaners, either, have no valving to permit interruption of the dispensing of the scent or provide valving downstream of the scent tablet so that scent dispenser, per se, must afford the totality of the valving for the dispenser. If the scent dispenser were to be utilized with a hard bag cleaner or a cleaner with a hard bag portion, the structure could be less complicated if a part of the valving was formed in the hard bag or hard bag portion, itself. This would simplify the added dispenser section and make valving more direct.

Accordingly, it is an advantage of the invention to form a portion of the scent dispensing arrangement in a hard bag or a hard bag portion of a vacuum cleaner.

It is an additional object of the invention to utilize a portion of the hard bag structure of a vacuum cleaner to form a valve part for the scent dispenser.

It is a further object of a invention to provide mounting for the scent dispenser slide in the hard bag portion of a vacuum cleaner.

It is a still further object of the invention to provide an inexpensive, operative scent dispensing arrangement.

It is an even further object of the invention to provide an improved scent dispensing arrangement.

SUMMARY OF THE INVENTION

The scent dispensing arrangement of this invention is formed of two elements, the requisite hard bag portion of a cleaner and the scent dispenser slide holder. This last element is mounted in an outwardly opening depression in the hard bag portion and includes an outer cover piece having a finger engaging central portion and an inner upwardly opening box or pocket for the reception and retention of the scent tablet. This pocket extends below a portion of the cover and is received in an inwardly horizontally extending slotted flange formed integrally with the hard bag portion. The tablet pocket is of less horizontal length than its slot so that the dispenser slide holder may reciprocally move relative to the hard bag portion. The scent dispenser tablet retaining pocket also has a rearwardly extending short guiding tab that engages in a horizontally extending elongated slot in the back wall of the depression in the hard bag portion. A top inwardly extending horizontal flange, forming the top side of the depression in the hard bag portion, is also apertured, with this aperture directing the outwardly moving suction airflow into the centered, scent retaining pocket and directly against the scent tablet to provide maximum dispensing. This aperture can also be placed in a less direct impinging relationship with the scent tablet by movement of the scent dispensing slide holder from its centered position to provide a much lesser level of dispensing. Dispensing, in all cases, is occasioned by the clearances between the parts which also permits easy sliding of the dispenser slide holder in the hard bag portion of the cleaner and its actual removal from it for the insertion of a new scent tablet.

BRIEF DESCRIPTION OF THE DRAWINGS

Reference may now be had to the accompanying Drawings for a better understanding of the invention, both as to its organization and function, with the illustration showing a preferred embodiment, but being only exemplary, and in which:

FIG. 1 is a front elevational view of a vacuum cleaner hard bag as modified by the present invention, the bag being shown as it may be carried by a vacuum cleaner handle configuration shown in ghost dot-dashed lines for the purpose of environment only;

FIG. 2 is an enlarged, partial front elevational view of the hard bag and scent dispenser comprising the invention but with its slide in an opposite position;

FIG. 3 is a front view similar to FIG. 2 but with the scent dispenser slide removed from the hard bag;

FIG. 4 is a back side or interior elevational view of the hard bag scent dispenser shown in FIG. 2 with the scent dispenser slide removed;

FIG. 5 is a partial side elevational view, in cross-section, of the hard bag as taken at line 5—5 of FIG. 4;

FIG. 6 is a front elevational view of a scent dispenser slide;

FIG. 7 is a rear elevational view of the scent dispenser slide;

FIG. 8 is a top plan view of the scent dispenser slide as taken from FIG. 7.

DETAILED DESCRIPTION OF THE INVENTION

Figure 9:
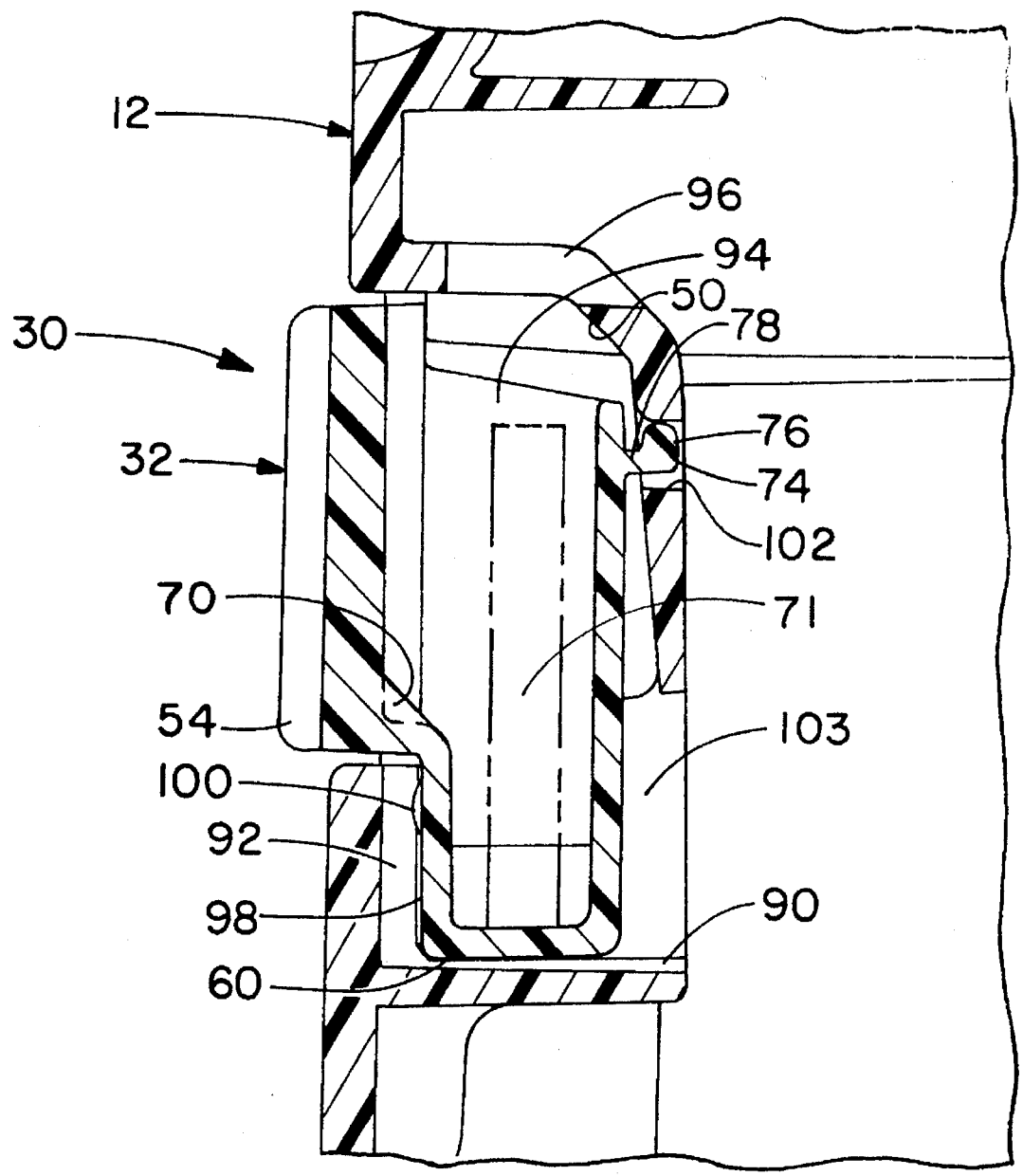
FIG. 9 is a cross-sectional elevational view of the scent dispenser and hard bag with the scent dispenser in its centered position.

There is shown in FIG. 1, a vacuum cleaner hard bag upper portion 10 which may comprise a dirt bag door 12 and an upper hard bag section 14. The upper hard bag section 14 is connected to a handle 16 while a motor fan system 18 is mounted to the hard bag upper portion at its bottom. The dirt bag door 12 may be conventionally hinged to hard bag upper portion 10 along a hinge line 20. Side hose supports 22, 24 may also be included integrally or attached to hard bag upper portion 10. The upper hard bag portion 10 also includes a latch 26 and provision for a full bag indicator 28. This full bag indicator forms no part of the invention.

A novel scent dispenser arrangement 30 is also included in hard bag portion 10. The scent dispenser arrangement 30 is formed partly in the dirt bag door 12 and partly by a scent dispenser slide 32, somewhat loosely mounted within the bag door 12.

The dirt bag door 12 and scent dispenser arrangement 30 includes a generally vertically stepped, horizontally elongated depression 34 having a flat back wall 36. This forms a major portion of the rear surface of stepped depression 34. It also includes upper and lower, elongated, inwardly horizontally extending flange walls 38, 40, respectively, joined to back wall 36. An end, flat short vertical wall 42 and a partially curvilinear vertical opposite wall 44 complete the depression 34. The flange walls 38 and 40 are provided with draft or tappered or slight angular disposition for easy withdrawal from their mold.

The step in stepped depression 34 is formed by the aforementioned back wall 36 and a rear bearing wall 46 outwardly displaced relative to back wall 36 and on which scent dispenser slide 32 slidingly moves. The bearing wall 46 is only slightly depressed from the surrounding surface of the dirt bag door 12 to provide the scent dispenser slide 32 a substantially flush relationship with this bag door surface which is streamlined around it. The shape of the depression 34 also depends on a relatively thin bearing flange 48 at the opposite end of the depression 34. This bearing flange is U-shaped and is bordered inwardly at its bight end by the curvilinear opposite wall 44. The bearing flange 48 also guides the scent dispenser slide 32 in its reciprocating movement since it is inset substantially to the level of inset formed by face 47 of rear bearing wall 46.

The back wall 36 of stepped depression 34 includes at its bottom side a short ramp section 50 (e.g. FIG. 9) that is shaped to move inwardly towards the center of depression 34 as it angles inwardly so that its bottom edge is on the same line as an inner line formed by the intersection of curvilinear wall 44 and back wall 36. This ramp joins to the upper flange wall 38 at its inner, lower side and aids in ease of molding and provides an upper guiding edge for scent dispenser slide 32. The bearing flange 48, as the bearing wall 46, are slightly inset relative to the surrounding surface of the dirt bag door 12 to provide for the thickness of the dispenser slide 32 so that a flush appearance for the scent dispenser arrangement 30 occurs.

The scent dispenser slide 32 includes an elongated medallion section 52 at its front that has a pair of horizontally medially disposed, slightly separate, vertically extending finger engaging portions 54, 54. These finger engaging portions are generally triangular in cross-section and provide a convenient means to permit grasping of the slide for manual manipulation. The medallion section 52 extends horizontally away from the finger engaging portions 54, 54 on each side to provide oppositely extending cover arms 56, 56 that terminate in curvilinear ends 58, 58. These also provide a pleasing appearance and meld into the curvilinear ends of stepped depression 34. The medallion section 52 is also slightly curved in plan view to meld into the steamlined curve of the dirt bag door 12.

On the rear side of the scent dispenser slide 32, is a well or U-shaped, open-bottomed box form 60, open at its top. This box form has the terminating legs of its U-shape integrally attached to a rear face 62 of the medallion section 52 which provides its fourth and front vertical side.

The box form 60 includes a lower projecting portion 64 extending below the medallion section 52 so that a large scent tablet 71 may be lodged in it. The projecting portion 64 has an internally thickened, lower front wall 66 extending fully across it and vertically upwardly, generally, to the medallion section 52 of the scent dispenser slide 32. In this portion it also has lower ribs 68, 68, of shorter height, extending rearwardly from the front wall 66 to a rearward wall 67 of the projecting portion 64. The thickened front wall 66 and ribs 68, 68 reinforce box form 60 in its lower reaches.

The top side of the front wall 66 includes a medially disposed, upwardly extending right angled ramp 70, triangularly shaped, with one of its apexes disposed against the rear face 62 of the box form 60 and with its base bearing against a top side of thickened wall 66. The scent tablet 71, of rounded wafer shape, may conveniently rest on a bottom floor 72 of projecting portion 64, behind front wall 66, and between the ribs 68, 68, receiving guidance to this location by ramp 70.

The scent dispenser slide 32 receives its sliding, reciprocating guidance in dirt bag door 12 by the lower projecting portion 64 of it and by an integral catch tab 74 extending rearwardly from the rear side of box form 60 of the scent dispenser slide 32. It is located near the top of the box form 60 and horizontally medially disposed relative to it. The catch tab is conventional and includes an inwardly extending tip 76 of somewhat ball-like, enlarged cross-section, integrally attached to a neck portion 78 of the catch tab 74. This portion, in turn, is integral with a rear face 80 of box form 60. The extending tip 76 of catch tab 74 is angled upwardly relative to its attachment to its neck portion 78.

The lower flange wall 40 of dirt bag door 12 is stepped downwardly at an inwardly extending curvilinear riser 80 (e.g., FIGS. 4 and 5) that is joined to a medially disposed, lower guide portion 82. It extends generally horizontally towards a second vertically extending curvilinear riser 84. This riser extends upwardly to the flat, short vertical wall 42 of step bearing wall 46. An open slot 88, opening upwardly and extending horizontally and inwardly between the back walls 36, the vertical termination 86 of rear bearing wall 46 and the inner termination of the lower flange wall 40, all of the formed depression 34 permits the downward insertion of the projecting portion 64 of box form 60 of scent dispenser 32 therein. It then abuts downwardly against a pair of inwardly extending upstanding ribs 90, 90, integral with the top face of guide portion 82. These ribs support the scent dispenser slide 32 and permits its easy reciprocation within depression 34.

A vertically extending center rib 92 is formed on a rear surface 93 of the bag door 12 immediately below the open slot 88. It serves as a detent for the centering of an open top 94 of box form 60 of scent dispenser slide 32 underneath an air discharge slot 96 of the scent dispensing arrangement 30. This slot is formed in bag door 12 medially in upper flange 38. It is centered on the center rib 92 so that, when detenting occurs, the discharge airflow passing through the air discharge slot 96 directly impinges on the inside of the center of the box-like form 60 and its included scent tablet 71.

Detenting of this scent dispensing slide 32 occurs because a front face 98 of the open box form 60 of the slide includes a pair of spaced nib-like outwardly extended rounded projections 100, 100. These projections are centered relative to the open box form 60 and also the finger projections 54, 54 and receive the center rib 92 therebetween when the scent dispensing slide 32 is properly detented.

A second guidance arrangement for the scent dispensing slide 32 is also afforded in the scent dispensing arrangement 30. It comprises an elongated horizontal medially disposed, slide guidance slot 102 formed in back wall 36 of depression 34. This slot receives the catch tab 74 therein, with the catch tip 76 engaging against a top surface of guidance slot 102 in back wall 34 in a resilient manner so that the scent dispenser slide 32 is captured between the catch tab 74 and the ribs 90, 90 engaging with the bottom of the open box form 60.

The bag door 12 also includes an open cutout 103 extending from a lower termination 106 of back wall 36 and a border afforded by the opposite risers 80, 84 and the guide portion 82 extending therebetween. This opening (open cutout 103) overlaps depression 34 in its lower reaches.

The scent dispenser slide 32 is easily assembled with the bag door 12 by first inserting the open box form 60 downwardly through the slot 88 and then pivoting the slide 32 inwardly into the depression 34 of the bag door 12. During this movement, the catch tab 74 resiliently cams downwardly as urged by the back wall 36 until it snaps into and against the top side of the guidance slot 102. Reversing the operation for disassembly, the catch tab 74 is again resiliently cammed out of the guidance slot 102 and the scent dispensing slide 32 removed outwardly from the bag door 12. Removal is facilitated if the slide is moved leftwardly in the depression 34 so that the operator's fingertips may more easily dislodge the slide 32.

When a scent tablet 71 is present in the open box form 60, with the scent dispenser slide 32 in its centered, detented position and the cleaner of which the bag door 12 is a part is operated, a good quantity of scent is dispensed. This is occasioned because the vacuum cleaner discharge air is medially, directly on the open box form 60 and its mounted scent tablet 71. The scented air moves from this direct, impinging relationship outwardly around the scent dispenser slide 32 through, for example, the cracks around its tip and sides since it is somewhat loosely mounted. When the scent dispenser slide 32 is not centrally detented (i.e., FIGS. 1 or 2), vacuum cleaner air discharge flow is not medial or centrally impinging on the open box form 60 so that air flowing outwardly through air discharge slot 96 reaches a somewhat lessened scent saturation. In this regard, it should be noted that a "scent" is always present around the instant scent dispensing cleaner, whether it is turned on or off, since a scent tablet is (perforce) volatile in nature and there is present no absolute seal between the hard bag portion, its scent tablet and the ambient surrounding air.

The full bag indicator 28 appears as a specialized mounting arrangement 104 in FIG. 2. This mounting arrangement forms no part of the invention.

It should be clear from the foregoing description that the objects of the invention set out for it have been fully satisfied. It should also be obvious that many modifications could be made to the described structure which would still fall within its spirit and purview.

What is claimed is:

1. A scent dispensing arrangement for a vacuum cleaner including:
   a) a hard bag housing door of said vacuum cleaner;
   b) a depression formed in said hard bag housing door and having an opening;
   c) a scent dispenser slide mounted generally outwardly of said hard bag door and being capable of reciprocatory motion in said depression;
   d) said scent dispenser slide including a medallion portion substantially covering said depression opening;
   e) said scent dispenser slide inwardly mounting a scent tablet;
   f) said scent dispenser serving to at least partially obscure said opening during portions of its said reciprocatory motion;
   g) a flow of vacuum cleaning exhaust air flowing to said scent tablet through an exit port in said hard bag housing to receive scent for its flow; and
   h) said scent dispensing arrangement having no external venting downstream of said scent tablet so that said scented exhaust flow solely escapes directly, closely around the perimeter said medallion portion.

2. A scent dispensing arrangement utilized with a vacuum cleaner including:
   a) a vacuum cleaner hard housing portion;
   b) an exhaust port in said hard housing portion for the discharge of cleaner suction air;
   c) a movable scent dispenser mounted movably in a depression formed in said hard housing portion;
   d) said movable scent dispenser disposed outwardly of said exit port and downstream thereof;
   e) a scent tablet disposed in a well in said scent dispenser;
   f) said exhaust port being disposed in said hard housing portion to open outwardly towards said well;
   g) said scent tablet being situatable centered directly adjacent said exhaust port in at least one position of said movable scent dispenser and offset from a centered relationship in at least one other position of said scent dispenser;
   i) said movable scent dispenser thereby providing a selected scent concentration flow of cleaner exhaust air to ambient by moving relative to said exhaust port to move said scent tablet relative to said exhaust port;
   j) whereby said discharge of suction cleaner air impinges directly outwardly on said scent tablet to a greater or lesser degree depending on the movable position of said scent dispenser within said depression.

3. The scent dispensing arrangement of claim 2 wherein:
   a) said movable scent dispenser arrangement may be moved in a reciprocating motion.

4. The scent dispensing arrangement of claim 2 wherein:
   a) said movable scent dispenser includes a covering medallion plate having at least one engaging portion engageable by a user's finger.

5. A scent dispensing arrangement for a vacuum cleaner including:
   a) a hard housing portion of said vacuum cleaner;
   b) a depression formed in said hard housing portion and having an opening;
   c) a scent dispenser slide mounted generally outwardly of said hard bag housing portion and being capable of reciprocating motion in said depression;
   d) said scent dispenser slide including a medallion portion substantially covering said depression opening;
   e) said scent dispenser slide mounting a scent tablet;
   f) said scent dispenser serving to at least partially obscure said opening during portions of said reciprocatory motion;
   g) said hard housing portion having an exit port;
   h) a flow of vacuum cleaning exhaust air flowing to said scent tablet through said exit port to receive scent for its flow; and
   i) said scent dispensing arrangement having no external venting so that said scented exhaust flow escapes solely around said medallion portion.

\* \* \* \* \*